US010591657B2

United States Patent
Kadokura et al.

(10) Patent No.: US 10,591,657 B2
(45) Date of Patent: Mar. 17, 2020

(54) OPTICAL FIBER LASER MODULE, LIGHTING DEVICE, AND TREATMENT DEVICE

(71) Applicant: SHIMADZU CORPORATION, Kyoto (JP)

(72) Inventors: Kazutomo Kadokura, Kyoto (JP); Mamoru Hisamitsu, Kyoto (JP); Kazuya Inoue, Kyoto (JP); Ryosuke Nishi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/098,445

(22) PCT Filed: May 18, 2016

(86) PCT No.: PCT/JP2016/064726
§ 371 (c)(1),
(2) Date: Nov. 2, 2018

(87) PCT Pub. No.: WO2017/199367
PCT Pub. Date: Nov. 23, 2017

(65) Prior Publication Data
US 2019/0094440 A1 Mar. 28, 2019

(51) Int. Cl.
*F21V 7/04* (2006.01)
*G01S 1/00* (2006.01)
(Continued)

(52) U.S. Cl.
CPC ........... *G02B 6/001* (2013.01); *A61N 5/0616* (2013.01); *F21K 9/60* (2016.08); *G02B 6/0006* (2013.01);
(Continued)

(58) Field of Classification Search
CPC ............ A61N 5/0616; A61N 2005/063; A61N 2005/0663; A61N 2005/0665;
(Continued)

(56) References Cited

U.S. PATENT DOCUMENTS

| 8,475,025 B2 | 7/2013 | Ott et al. |
| 2010/0066254 A1 | 3/2010 | Ott et al. |

FOREIGN PATENT DOCUMENTS

| CN | 101568865 | 10/2009 |
| JP | 2003010205 | 1/2003 |

(Continued)

OTHER PUBLICATIONS

"International Preliminary Report On Patentability Of PCT/JP2016/064726", this report contains the following items: Form PCT/IB/373, PCT/ISA237(cover sheet), PCT/ISA237(Box No. I), and PCT/ISA237(Box No. V), dated Nov. 20, 2018, which is English translation of "Written Opinion of the International Searching Authority", pp. 1-10.

(Continued)

*Primary Examiner* — Jason M Han
(74) *Attorney, Agent, or Firm* — JCIPRNET (57) ABSTRACT

An optical fiber laser module is provided with an optical fiber (2) for diffusing light, and a laser module housing (1) connected to the optical fiber. The laser module housing is provided with a laser light source (11) that outputs laser light to the optical fiber, and a light detector (14) that detects laser light that has been wave-guided through the full length of the optical fiber. The optical fiber is provided with: a light incident part (3a) provided inside the laser module housing, laser light from the laser light source being incident on the light incident part; and a terminal part (3) on which is formed a reflective film (4) that reflects the laser light that was incident on the light incident part and was wave-guided (Continued)

through the full length of the optical fiber so as to return the laser light to the light incident part.

7 Claims, 5 Drawing Sheets

(51) Int. Cl.
    *G09B 9/00*     (2006.01)
    *H01S 3/00*     (2006.01)
    *H01S 3/30*     (2006.01)
    *F21V 8/00*     (2006.01)
    *A61N 5/06*     (2006.01)
    *F21K 9/60*     (2016.01)
    *A61N 5/067*     (2006.01)
    *G02B 6/42*     (2006.01)
    *H01S 3/13*     (2006.01)
    *H01S 3/23*     (2006.01)

(52) U.S. Cl.
    CPC .. *A61N 2005/063* (2013.01); *A61N 2005/067* (2013.01); *A61N 2005/0663* (2013.01); *A61N 2005/0665* (2013.01); *G02B 6/4215* (2013.01); *G02B 6/4286* (2013.01); *H01S 3/1305* (2013.01); *H01S 3/2391* (2013.01)

(58) Field of Classification Search
    CPC .. A61N 2005/067; F21K 9/60; G02B 6/0006; G02B 6/001; G02B 6/4215; G02B 6/4286; H01S 3/1305; H01S 3/2391
    USPC .................................................. 362/551–582
    See application file for complete search history.

(56) References Cited

FOREIGN PATENT DOCUMENTS

| | | |
|---|---|---|
| JP | 2006292424 | 10/2006 |
| JP | 2014220245 | 11/2014 |

OTHER PUBLICATIONS

"Office Action of China Counterpart Application," with English translation thereof, dated Oct. 11, 2019, p. 1-p. 13.

OPTICAL FIBER LASER MODULE, LIGHTING DEVICE, AND TREATMENT DEVICE

CROSS-REFERENCE TO RELATED APPLICATION

This application is a 371 application of the International PCT application serial no. PCT/JP2016/064726, filed on May 18, 2016. The entirety of each of the above-mentioned patent applications is hereby incorporated by reference herein and made a part of this specification.

BACKGROUND

Technical Field

The disclosure relates to an optical fiber laser module with an optical fiber connected to a laser light source, a lighting device, and a treatment device, in particular, to a structure of the optical fiber laser module utilizing diffusion and light emission from the optical fiber.

Description of Related Art

The optical fiber laser module with an optical fiber connected to a laser light source is widely used. Furthermore, in recent years, laser lighting utilizing light emission from optical fiber has been proposed as the next generation light source for illumination.

Specifically, the light diffusing fiber "Fibrance" manufactured by Corning can be combined with a desired laser light source to be used for laser lighting. The "Fibrance" light diffusing fiber has a structure that diffuses about 90% of the laser light incident into the fiber from the periphery of the fiber to the outside. Besides, the remaining 10% of the laser light, which is not diffused, is emitted from an optical fiber emitting part to the outside.

The light emitting device described in Patent Document 1 is known as a lighting device using the light diffusing fiber. In order to prevent dangerous laser light from being radiated to the outside when the optical fiber is damaged, a detector is provided in the optical fiber emitting part of the light emitting device, which controls driving of the laser light source according to the light intensity detected by the detector.

RELATED ART

Patent Document

[Patent Document 1] Japanese Laid-Open No. 2014-220245

SUMMARY

Technical Problem

However, the light emitting device described in Patent Document 1 has the following problem. That is, external parts, such as the detector, which cannot be used for lighting are provided at the front end of the optical fiber. In other words, appearance wise, it is necessary to consider a configuration of the detector which does not interfere with lighting or the light emitting device.

In addition, when laser coupling from the laser light source to the optical fiber is 90% and the diffusion efficiency of the optical fiber is 90%, the whole utilization efficiency of the laser light is 81%.

The disclosure provides a safe and compact optical fiber laser module which can utilize laser light more efficiently without any light detector interfering with lighting, a lighting device, and a treatment device.

Solutions to the Problem

In view of the above, an optical fiber laser module of the disclosure includes an optical fiber which diffuses light; and a laser module housing connected to the optical fiber, wherein the laser module housing includes a laser light source outputting a laser light to the optical fiber; and a light detector detecting the laser light wave-guided through a full length of the optical fiber.

In addition, the optical fiber includes a light incident part on one end and a terminal part on the other end, wherein the light incident part is guided into the laser module housing and the laser light from the laser light source is incident on the light incident part, and the terminal part is formed with a reflective part that reflects the laser light incident on the light incident part and wave-guided through the full length of the optical fiber, and returns the laser light to the light incident part.

Effects

According to the optical fiber laser module of the disclosure, since the light detector is provided in the laser module housing, the light detector does not interfere with lighting. Also, it is possible to use the entire area of the optical fiber outside the laser module housing as an emission light source, and the light source can be handled as a clear light emitting part without any mechanical part.

In addition, since a reflective film reflects the laser light incident on the light incident part and wave-guided through the full length of the optical fiber, and returns the laser light to the light incident part, the utilization efficiency of the returning laser light can be improved. Accordingly, a safe and compact optical fiber laser module which can utilize laser light more efficiently, a lighting device, and a treatment device can be provided.

BRIEF DESCRIPTION OF THE DRAWINGS (a) of FIG. 1 is a configuration diagram of an optical fiber laser module according to Embodiment 1, and (b) of FIG. 1 is a schematic view of a light diffusing fiber of the optical fiber laser module according to Embodiment 1.

DESCRIPTION OF THE EMBODIMENTS

Hereinafter, an optical fiber laser module according to the embodiments of the disclosure will be described in details with reference to the drawings.

Embodiment 1

Figure 1:
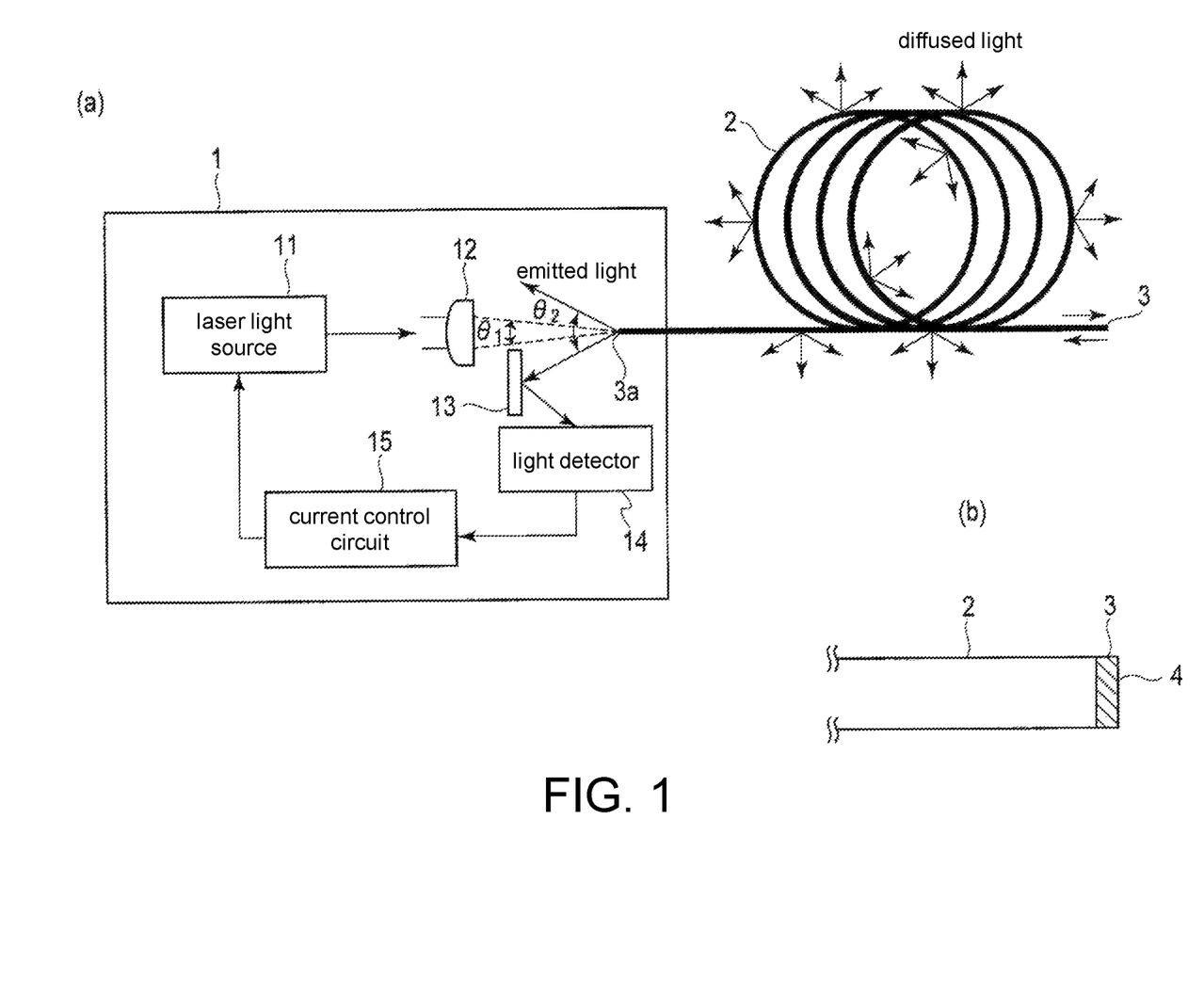

(a) of FIG. 1 is a configuration diagram of an optical fiber laser module according to Embodiment 1, and (b) of FIG. 1 is a schematic view of a light diffusing fiber of the optical fiber laser module according to Embodiment 1. The optical fiber laser module shown in FIG. 1 includes a light diffusing fiber 2 and a laser module housing 1 connected to the light diffusing fiber 2.

The laser module housing 1 has a laser light source 11, a condenser lens 12, a mirror 13, a light detector 14, and a current control circuit 15. The laser light source 11 outputs a laser light to the condenser lens 12. The condenser lens 12 condenses the laser light from the laser light source 11 at an incident angle $\theta_1$ and guides the laser light to a light incident part 3a of the light diffusing fiber 2. That is, the laser light is optically coupled into the light diffusing fiber 2 connected to the laser module housing 1.

One end of the light diffusing fiber 2 includes the light incident part 3a which is guided into the laser module housing 1 and to which the laser light from the laser light source 11 is incident. Another end of the light diffusing fiber 2 includes a terminal part 3 formed with a reflective film 4. The reflective film 4 reflects the laser light incident on the light incident part 3a and wave-guided through the full length of the optical fiber, and returns the laser light to the light incident part 3a. The light diffusing fiber 2 diffuses the laser light incident on the light incident part 3a. For example, the light diffusing fiber 2 diffuses 90% of the laser light incident on the light incident part 3a to the outside and guides the remaining 10% to the terminal part 3 of the light diffusing fiber 2.

The reflective film 4 (corresponding to the reflective part of the disclosure), which has a high reflectance R with respect to any wavelength, reflectance R=99.9% for example, is applied to the terminal part 3, so as to reflect the wave-guided light from the light diffusing fiber 2. The reflective film 4 is formed of a laminate of dielectric thin films of $SiO_2$ film and $Ta_2O_5$ film, for example.

Furthermore, in addition to coating with the reflective film 4, a mirror with a filter that transmits a specific wavelength may be included as a modified example.

The angle of the laser light emitted from the light incident part 3a is $\theta_2$, and the emission angle $\theta_2$ of the emitted light is larger than the incident angle $\theta_1$. Therefore, the numerical aperture NA2 is set to be larger than the numerical aperture NA1.

The mirror 13 reflects the emitted light from the light incident part 3a and guides the light to the light detector 14. The light detector 14 is composed of a photodiode for example and detects the light intensity of the laser light wave-guided through the full length of the light diffusing fiber 2.

The current control circuit 15 controls the drive current flowing to the laser light source 11 according to the light intensity detected by the light detector 14. For example, when the light diffusing fiber 2 is damaged or disconnected, the light intensity decreases markedly. Therefore, the current control circuit 15 compares the amount of light intensity change detected by the light detector 14 with a preset value to determine that the light diffusing fiber 2 is abnormal, and stops the drive current from driving the laser light source 11, thus stopping the laser light from the laser light source 11.

According to the configuration of the optical fiber laser module of Embodiment 1 as described above, the light diffusing fiber 2 diffuses 90% of the laser light incident on the light incident part 3a to the outside and reflects the remaining 10% of the laser light by the reflective film 4 applied to the terminal part 3 of the light diffusing fiber 2 and reciprocates the laser light inside the light diffusing fiber 2, so as to use it for light diffusion. For this reason, 99% of the coupled laser light can be used and efficiency can be improved.

Furthermore, since the light detector 14 is provided in the laser module housing 1, the light detector 14 does not interfere with lighting and it is possible to use the entire area of the optical fiber outside the laser module housing 1 as an emission light source, and the light source can be handled as a clear light emitting part without any mechanical part.

Therefore, a safe and compact optical fiber laser module which can utilize laser light with a higher efficiency can be provided.

Embodiment 2

Figure 2:
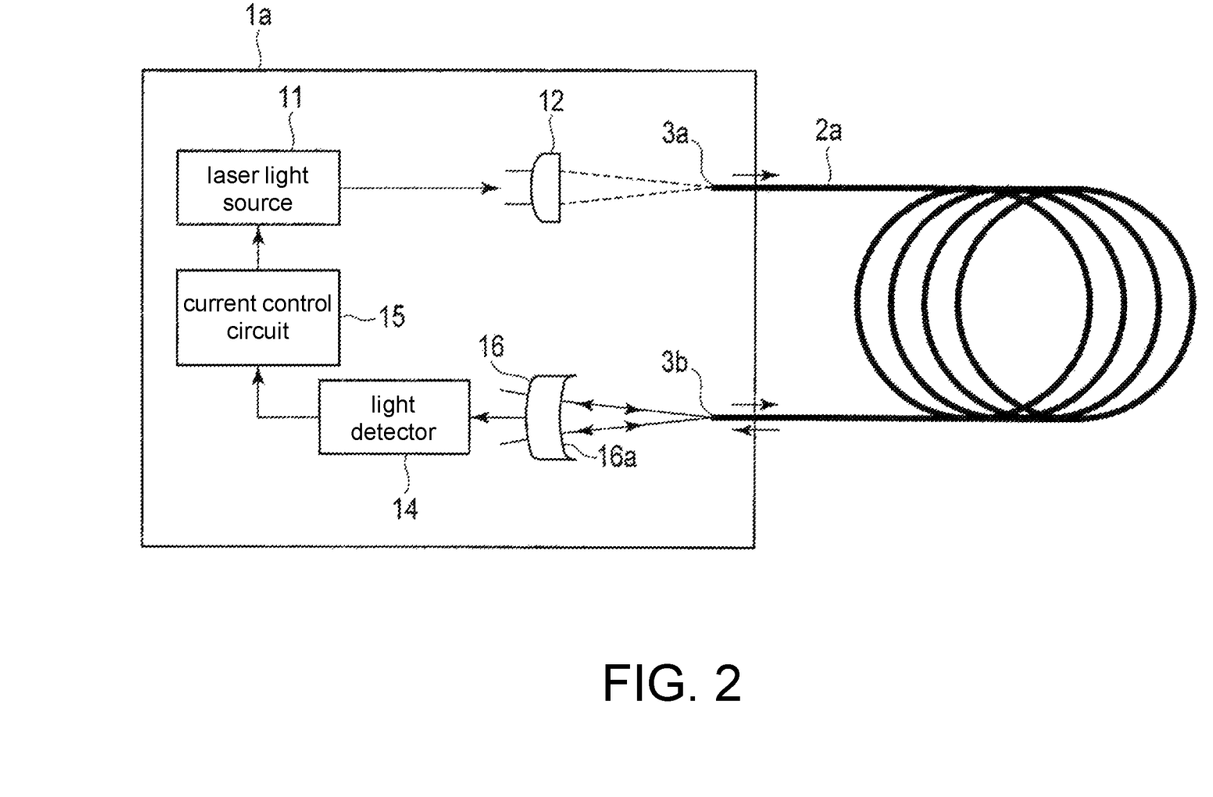
FIG. 2 is a configuration diagram of an optical fiber laser module according to Embodiment 2.

FIG. 2 is a configuration diagram of an optical fiber laser module according to Embodiment 2. The optical fiber laser module of Embodiment 2 shown in FIG. 2 is characterized by using a U-shaped light diffusing fiber 2a having a light incident part 3a and a light emitting part 3b. The light incident part 3a and the light emitting part 3b are provided in the laser module housing 1a.

The laser light from the laser light source 11 is incident on the light incident part 3a via the condenser lens 12. The light emitting part 3b emits the laser light incident on the light incident part 3a and wave-guided through the full length of the light diffusing fiber.

In addition, the laser module housing 1a has a concave mirror 16. The concave mirror 16 corresponds to the reflective member of the disclosure, and a reflective film 16a is applied to the concave portion. The concave mirror 16 reflects the laser light from the light emitting part 3b via the reflective film 16a and returns the laser light to the light incident part 3a via the light emitting part 3b. The reflectance of the reflective film 16a is 99.9% for example. The concave mirror 16 outputs a portion of the laser light from the light emitting part 3b to the light detector 14.

Since the operations and functions of the light detector 14 and the current control circuit 15 are the same as shown in FIG. 1, the descriptions thereof will be omitted.

According to the configuration of the optical fiber laser module of Embodiment 2 as described above, the light diffusing fiber 2a diffuses 90% of the laser light incident on the light incident part 3a to the outside and emits the remaining 10% from the light emitting part 3b of the light diffusing fiber 2a.

Then, the laser light emitted from the light emitting part 3b is reflected by the concave mirror 16 and reciprocated inside the light diffusing fiber 2a. Therefore, since the reciprocated laser light can be used for light diffusion, 99% of the coupled laser light can be used and efficiency can be improved. Therefore, the optical fiber laser module of Embodiment 2 can also obtain the same effects as the optical fiber laser module of Embodiment 1.

In addition, since two ends of the light diffusing fiber 2a have the light incident part 3a and the light emitting part 3b respectively, it is possible to adopt the laser light incidence method at both ends and obtain the amount of light corresponding to 2 units of laser light sources.

In addition, the optical fiber laser module of Embodiment 2 is suitable as a safety measure when the laser light intensity is so high that the laser light passes through the reflective film 4 of the optical fiber laser module of Embodiment 1.

In addition to the method of detecting the laser light with the light detector 14 shown in FIG. 2, light diffused around the terminal part of the light diffusing fiber 2a may also be detected.

Embodiment 3

Figure 3:
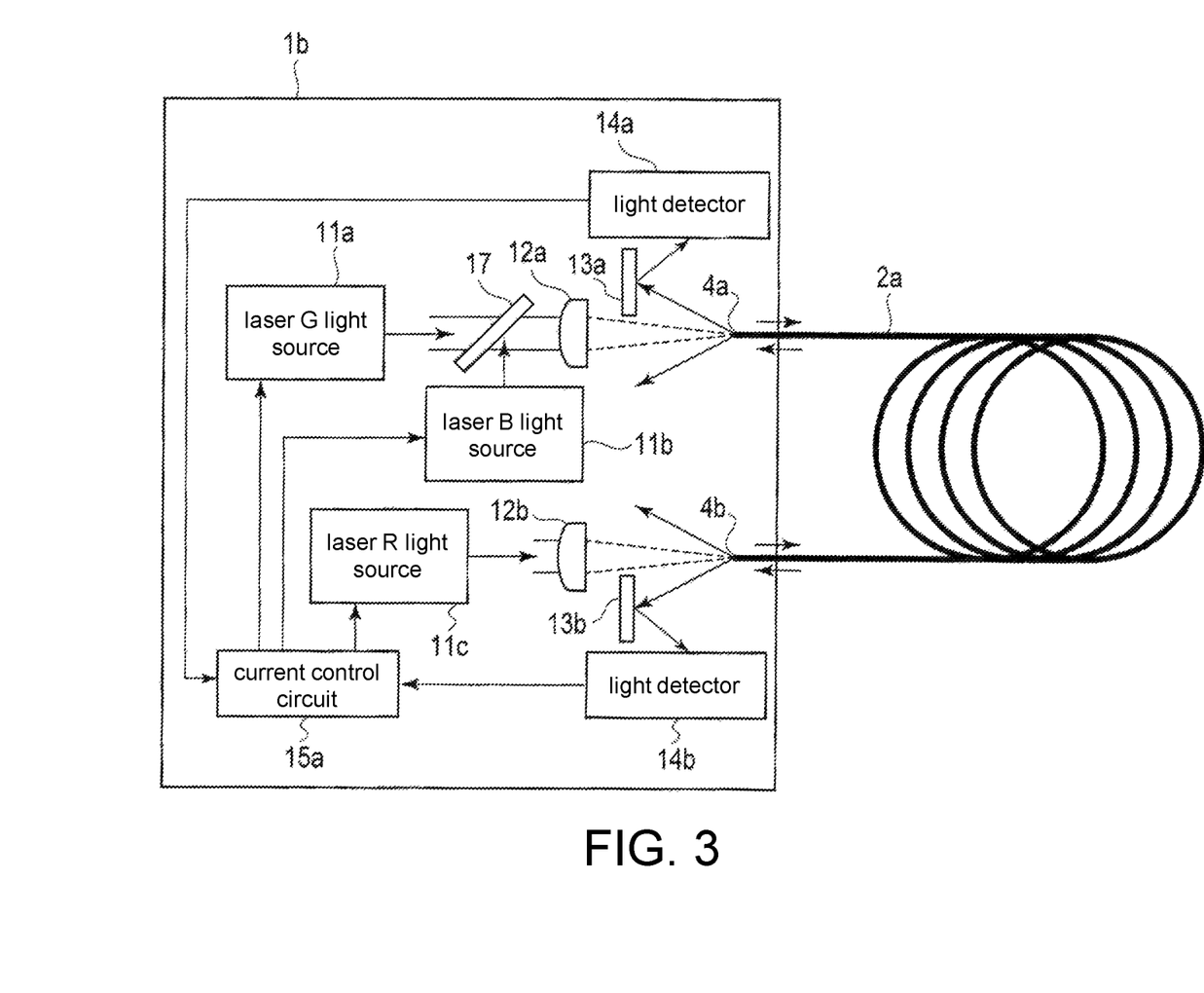
FIG. 3 is a configuration diagram of an optical fiber laser module according to Embodiment 3.

FIG. 3 is a configuration diagram of an optical fiber laser module according to Embodiment 3. The laser module housing 1b shown in FIG. 3 includes a laser R light source (red light source) 11c, a laser G light source (green light source) 11a, a laser B light source (blue light source) 11b, condenser lenses 12a and 12b, mirrors 13a and 13b, light detectors 14a and 14b, a current control circuit 15a, and a mirror 17.

The light diffusing fiber 2a is U-shaped and includes a first incident end part 4a and a second incident end part 4b. The first incident end part 4a and the second incident end part 4b are provided in the laser module housing 1b.

In order to obtain a white light, the laser R light source 11c, the laser G light source 11a, and the laser B light source 11b, which serve as the laser light source, are optically coupled to the light diffusing fiber 2a.

The laser G light source 11a has a wavelength λ of 532 nm and outputs a green laser light to the condenser lens 12a via the mirror 17. The laser B light source 11b has a wavelength λ, of 450 nm and outputs a blue laser light to the condenser lens 12a via the mirror 17. The condenser lens 12a condenses the green laser light and the blue laser light from the mirror 17 and guides them to the first incident end part 4a.

The laser R light source 11c has a wavelength λ of 640 nm and outputs a red laser light to the condenser lens 12b. The condenser lens 12b condenses the red laser light from the laser R light source 11c and guides it to the second incident end part 4b. Each of the light sources 11a to 11c can use a laser diode or a solid state laser, so as to obtain light of a desired wavelength band.

The light detector 14a detects the light intensity of the laser light from the light diffusing fiber 2a via the mirror 13a. The light detector 14b detects the light intensity of the laser light from the light diffusing fiber 2a via the mirror 13b.

According to the light intensity of the laser light from the light detector 14a and the light intensity of the laser light from the light detector 14b, the current control circuit 15a controls the drive current flowing to the laser G light source 11a, the laser B light source 11b, and the laser R light source 11c.

According to the configuration of the optical fiber laser module of Embodiment 3 as described above, the green laser light from the laser G light source 11a and the blue laser light from the laser B light source 11b are incident on the first incident end part 4a and diffused by the light diffusing fiber 2a. Also, the red laser light from the laser R light source 11c is incident on the second incident end part 4b and is diffused by the light diffusing fiber 2a. Therefore, the white light is obtained.

Also, in the case of the laser G light source 11a, the laser B light source 11b, and the laser R light source 11c of Embodiment 3, considering the aberration when converging light due to wavelength, the light sources are divided into the laser G light source 11a and the laser B light source 11b, and the laser R light source 11c with small wavelength differences and coupled into the light diffusing fiber 2a. With such configuration, it is possible to improve the efficiency of coupling into the light diffusing fiber 2a.

Besides, a combination of close wavelengths may be used, and the light sources may be divided into the laser G light source 11a and the laser R light source 11c, and the laser B light source 11b to be coupled into the light diffusing fiber 2a.

Also, the light diffusing fiber 2a is folded back at the terminal parts, the first incident end part 4a and the second incident end part 4b, so as to increase the utilization efficiency of the final light.

Besides, light detection may be carried out by a light detector at one location, or by a plurality of light detectors corresponding to RGB wavelengths.

Embodiment 4

Figure 4:
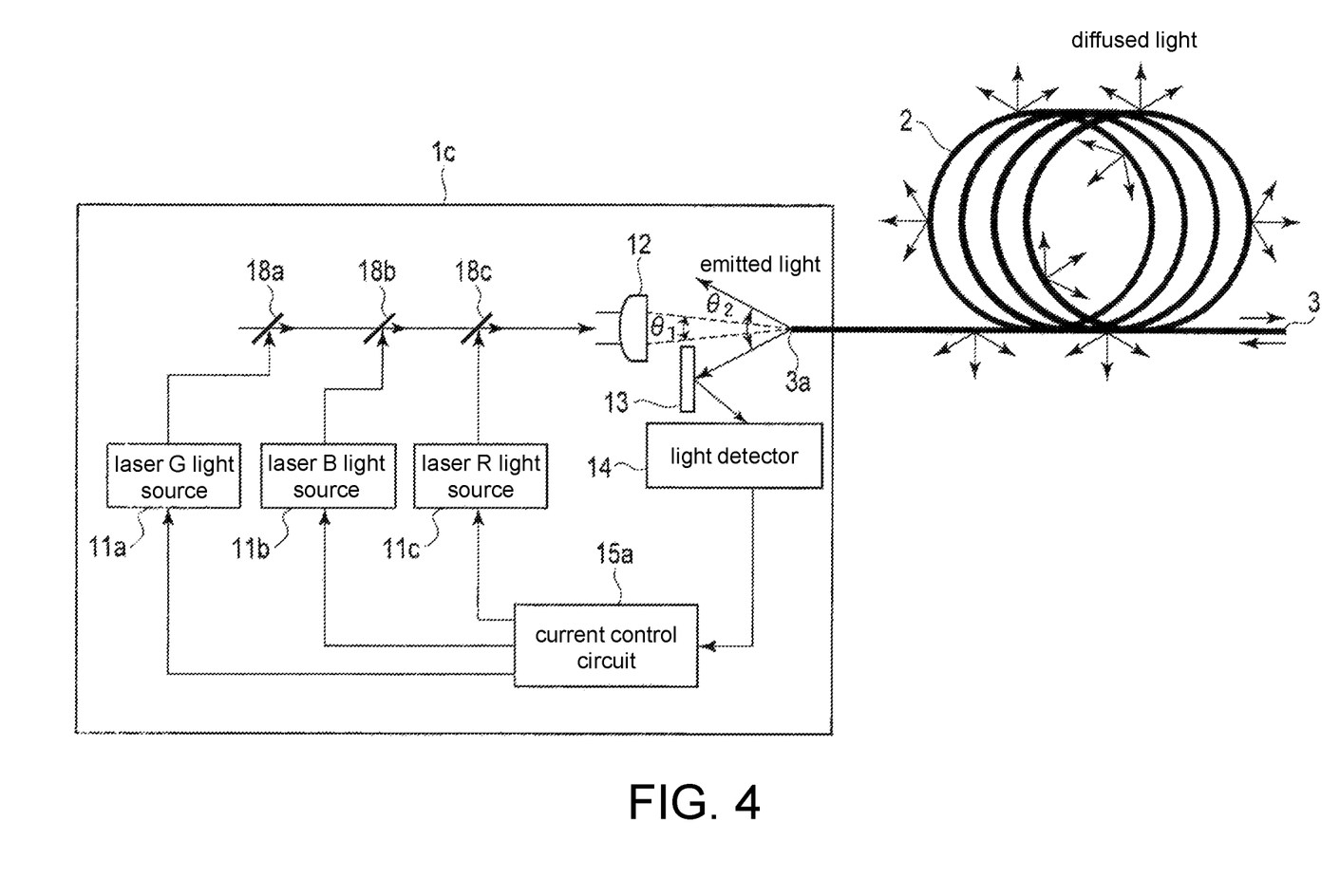
FIG. 4 is a configuration diagram of an optical fiber laser module according to Embodiment 4.

FIG. 4 is a configuration diagram of an optical fiber laser module according to Embodiment 4. The optical fiber laser module 1c of Embodiment 4 further includes a laser R light source 11c, a laser G light source 11a, a laser B light source 11b, and mirrors 18a to 18c in the laser module housing of the optical fiber laser module of Embodiment 1.

The mirrors 18a to 18c are provided on the central axis of the condenser lens 12. The mirror 18a reflects the green laser light from the laser G light source 11a and outputs the green laser light to the condenser lens 12 via the mirrors 18b and 18c. The mirror 18b reflects the blue laser light from the laser B light source 11b and outputs the blue laser light to the condenser lens 12 via the mirror 18c. The mirror 18c reflects the red laser light from the laser R light source 11c and outputs the red laser light to the condenser lens 12.

The condenser lens 12 makes the red laser light, the green laser light, and the blue laser light incident on the light diffusing fiber 2.

Therefore, the optical fiber laser module of Embodiment 4 can also obtain the same effects as the optical fiber laser modules of Embodiments 1 and 3.

Embodiment 5

Figure 5:
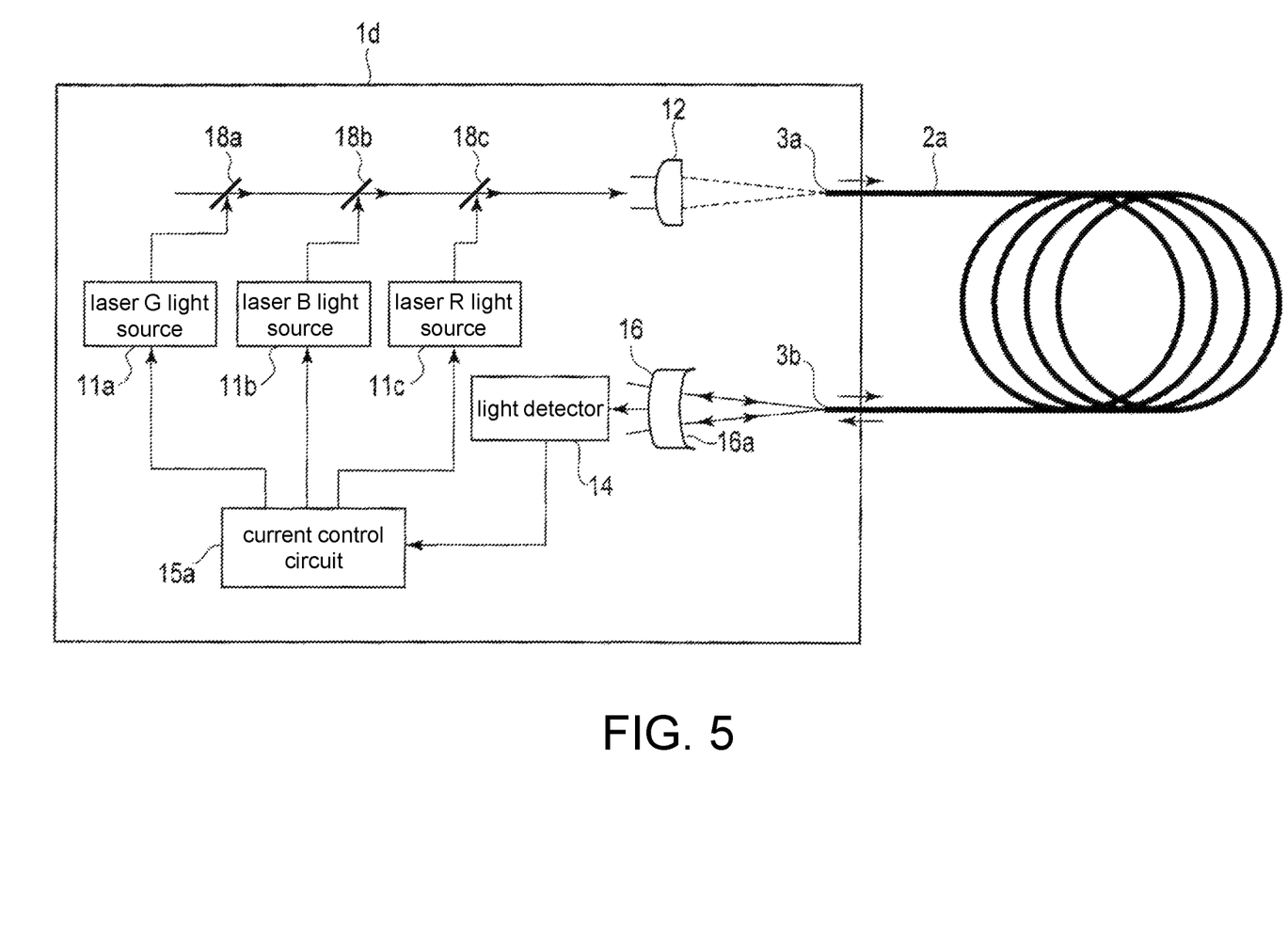
FIG. 5 is a configuration diagram of an optical fiber laser module according to Embodiment 5.

FIG. 5 is a configuration diagram of an optical fiber laser module according to Embodiment 5. The optical fiber laser module 1d of Embodiment 5 further includes a laser R light source 11c, a laser G light source 11a, a laser B light source 11b, and mirrors 18a to 18c in the laser module housing of the optical fiber laser module of Embodiment 2.

The mirrors 18a to 18c are provided on the central axis of the condenser lens 12. The mirror 18a reflects the green laser light from the laser G light source 11a and outputs the green laser light to the condenser lens 12 via the mirrors 18b and 18c. The mirror 18b reflects the blue laser light from the laser B light source 11b and outputs the blue laser light to the condenser lens 12 via the mirror 18c. The mirror 18c reflects the red laser light from the laser R light source 11c and outputs the red laser light to the condenser lens 12.

The condenser lens 12 makes the red laser light, the green laser light, and the blue laser light incident on the light diffusing fiber 2a.

Therefore, the optical fiber laser module of Embodiment 5 can also obtain the same effects as the optical fiber laser modules of Embodiments 2 and 3.

Also, in the optical fiber laser modules of Embodiments 1 to 5, it is favorable to use a connector with a safety shutter for attaching and detaching of the optical fiber as the connecting part between the laser module housing 1 and the light diffusing fiber 2. Furthermore, it is favorable to use a non-powered connector making use of fiber bending.

(Various Devices Using Optical Fiber Laser Module)

The lighting device, which is provided with the optical fiber laser module in the disclosure and uses the diffused light from the light diffusing fiber 2 for lighting, can maintain safety while realizing a compact device with high utilization efficiency.

The lighting device can be used as illumination, etc. for commercial or construction applications, industrial applications (lighting for work support), lighting for medical applications as a type of laser treatment device for therapy of atopic dermatitis treatment, etc.

Next, the configurations of the lighting device and the treatment device using the optical fiber laser module will be described.

The lighting device has a laser module housing 1 and a light diffusing fiber 2. The treatment device has a laser module housing 1, a light diffusing fiber 2, and a laser treatment part (not shown). The laser treatment part treats a treatment target using a laser light outputted from the light diffusing fiber 2.

INDUSTRIAL APPLICABILITY

The disclosure can be applied to laser lighting devices, laser treatment devices and the like.

What is claimed is:

1. An optical fiber laser module, comprising:
    an optical fiber which diffuses light; and
    a laser module housing connected to the optical fiber, wherein
    the laser module housing comprises:
    a laser light source outputting a laser light to the optical fiber; and
    a light detector is configured inside the laser module housing to detect the laser light wave-guided through a full length of the optical fiber.

2. The optical fiber laser module according to claim 1, wherein the optical fiber comprises:
    a light incident part on one end, wherein the light incident part is guided into the laser module housing and the laser light from the laser light source is incident on the light incident part; and
    a terminal part on the other end, wherein the terminal part is formed with a reflective part that reflects the laser light incident on the light incident part and wave-guided through the full length of the optical fiber, and returns the laser light to the light incident part.

3. The optical fiber laser module according to claim 2, wherein the laser light source comprises a red light source, a green light source, and a blue light source, wherein the laser light of each light source is incident on the light incident part.

4. The optical fiber laser module according to claim 1, wherein the optical fiber comprises:
    a light incident part on which the laser light from the laser light source is incident; and
    a light emitting part emitting the laser light incident on the light incident part and wave-guided through the full length of the optical fiber, and
    the laser module housing comprises the light incident part, the light emitting part, and a reflective member for reflecting the laser light from the light emitting part and returning the laser light to the light incident part via the light emitting part.

5. The optical fiber laser module according to claim 1, wherein the optical fiber comprises a first incident end part and a second incident end part provided in the laser module housing,
    the laser light source comprises a red light source, a green light source, and a blue light source, and
    the laser light of any one of the red light source, the green light source, and the blue light source is incident on the first incident end part, and the laser lights of the remaining light sources excluding the any one of the red light source, the green light source, and the blue light source are incident on the second incident end part.

6. A lighting device comprising the optical fiber laser module according to claim 1.

7. A treatment device, comprising:
    the optical fiber laser module comprising the optical fiber according to claim 1; and
    a laser treatment part treating a treatment target using a laser light outputted from the optical fiber.

* * * * *